United States Patent
Kraft et al.

(10) Patent No.: US 11,547,770 B2
(45) Date of Patent: Jan. 10, 2023

(54) UV EMITTER MODULE AND USE THEREOF

(71) Applicant: Heraeus Noblelight GmbH, Hanau (DE)

(72) Inventors: Johannes Kraft, Linsengericht (DE); Silke Schloemp, Dortmund (DE); Jan Winderlich, Hanau (DE)

(73) Assignee: HERAEUS NOBLELIGHT GMBH, Hanau (DE)

( * ) Notice: Subject to any disclaimer, the term of this patent is extended or adjusted under 35 U.S.C. 154(b) by 88 days.

(21) Appl. No.: 16/961,708

(22) PCT Filed: Dec. 10, 2018

(86) PCT No.: PCT/EP2018/084078
§ 371 (c)(1),
(2) Date: Jul. 13, 2020

(87) PCT Pub. No.: WO2019/154542
PCT Pub. Date: Aug. 15, 2019

(65) Prior Publication Data
US 2021/0361792 A1    Nov. 25, 2021

(30) Foreign Application Priority Data
Feb. 9, 2018    (DE) .................. 10 2018 102 928.4

(51) Int. Cl.
*H01J 61/72*    (2006.01)
*A61L 2/10*    (2006.01)
*H01J 61/52*    (2006.01)

(52) U.S. Cl.
CPC .............. *A61L 2/10* (2013.01); *H01J 61/523* (2013.01); *H01J 61/72* (2013.01)

(58) Field of Classification Search
CPC ...... A61L 2/10; A61L 2202/11; H01J 61/523; H01J 61/72
(Continued)

(56) References Cited

U.S. PATENT DOCUMENTS

2015/0283279 A1*  10/2015  Lott .................. G01F 1/76
250/428

FOREIGN PATENT DOCUMENTS

CN    204760737    11/2015
DE    202013000809    3/2013
(Continued)

OTHER PUBLICATIONS

German Office Action dated Oct. 25, 2018 in corresponding German Patent Application No. 102018102928.4.
(Continued)

*Primary Examiner* — Michael Maskell
(74) *Attorney, Agent, or Firm* — Panitch Schwarze Belisario & Nadel LLP

(57) ABSTRACT

UV lamp modules for the ultraviolet irradiation of a substrate. The modules include multiple low-pressure mercury lamps, each having a longitudinal axis, located in a waterproof housing having a bottom, a top and a beam exit opening in the bottom which is closed by a beam exit window. To maintain hygiene, homogeneity and compactness, a first airflow zone for the supply of cooling air and a second, separate airflow zone for the discharge of heated cooling air are formed iii the housing. Viewed in a cross-section through the housing perpendicular to the longitudinal axes of the lamps and in a viewing direction from the bottom to the top, the beam exit window, the lamps and the airflow zones are arranged one after the other. The first airflow zone comprises an air supply duct which is equipped with at least one air-guiding mechanism for supplying cooling air to the lamps.

19 Claims, 2 Drawing Sheets

(58) Field of Classification Search
USPC .................................. 250/453.11–455.11
See application file for complete search history.

(56) References Cited

FOREIGN PATENT DOCUMENTS

| DE | 202017101112 | | 5/2017 | | |
|----|----|----|----|----|----|
| EP | 0985121 | | 3/2000 | | |
| EP | 2775195 | | 9/2014 | | |
| EP | 2926838 | | 10/2015 | | |
| EP | 2926838 | A1 * | 10/2015 | ............... | A61L 2/10 |
| EP | 3192588 | | 7/2017 | | |
| JP | S60092535 | U | 6/1985 | | |
| WO | 2014059567 | | 4/2014 | | |

OTHER PUBLICATIONS

International Search Report and Written Opinion dated Apr. 2, 2019 for corresponding International Patent Application No. PCT/EP2018/084078.

Notice of Reasons for Refusal for Japanese Patent Application No. 2020-542444, dispatch dated Aug. 3, 2022 (machine-generated English translation of examination report).

* cited by examiner

UV EMITTER MODULE AND USE THEREOF

CROSS REFERENCE TO RELATED APPLICATIONS

This application is a U.S. National Phase filing of International Patent Application No. PCT/EP2018/084078 filed on Dec. 10, 2018, which claims the priority of German Patent Application No. 102018102928.4 filed on Feb. 9, 2018. The disclosures of these applications are hereby incorporated by reference in their entirety.

TECHNICAL FIELD

The present invention relates to an ultraviolet (UV) lamp module for the ultraviolet irradiation of a substrate, with a waterproof housing surrounding a lamp arrangement that comprises multiple low-pressure mercury lamps each having a longitudinal axis, and having a bottom side, a top side and at least two side walls connecting the bottom side and the top side to each other, and a beam exit opening on the bottom side, which is closed by a beam exit window.

Furthermore, the invention relates to a use of the lamp module.

UV lamp modules are employed, e.g., in air-conditioning and drinking water systems, and in food production, for decontamination. Foodstuffs such as fruit and vegetables are irradiated, as well as machine parts, packaging materials, liquids, air and surfaces coming into contact with the foodstuffs during preparation. Microorganisms such as pathogens, in particular bacteria or viruses, are inactivated by the ultraviolet radiation.

Disinfection and sterilization are distinguished by the reduction in microbial load determined in specific test methods, or by the number of living individuals. Disinfection is where the microbial load has been reduced to at least $10^{-5}$, and for sterilization a reduction in the number of living individuals by at least six powers of ten ($10^{-6}$) is required. Regardless of the degree of reduction in microbial load, the generic term "decontamination" is used here and below.

UV lamps that are suitable for decontamination are, for example, mercury vapor discharge lamps, which can be configured as low-pressure lamps, medium-pressure lamps or high-pressure lamps. Mercury vapor discharge lamps in their elongated version have a cylindrical lamp tube made of fused silica with two electrodes arranged therein. The lamp tube is sealed at both ends in a gas-tight manner, e.g., by a pinch seal, through which a power supply is fed for the electrical bonding of the electrodes. The filling gas is mercury and generally a noble gas. In addition, a mercury deposit, which can consist of pure mercury or a mercury amalgam, is often inserted in the lamp tube. Mercury vapor discharge lamps have an emission spectrum with characteristic lines at 254 nm (UV C radiation) and possibly 185 nm (VUV radiation).

With regard to their suitability for various environmental conditions, lamp modules are classified based on guidelines for the degree of sealing (degree of protection) that the lamp module housing must have. They are categorized by so-called IP codes (International Protection Codes) with two-digit code numbers. The first code digit relates to the degree of protection against foreign bodies, such as dust particles; the second code digit indicates the degree of protection against water.

If lamp modules with UV lamps are employed. e.g., for disinfecting containers or packaging for food, they must be accommodated in a housing that is dust-tight; the first IP code digit in that case, for example, is 6. In addition, the housing must offer protection against the ingress of a cleaning fluid, such as water, hydrogen peroxide or sodium hydroxide solution, this being expressed by the second code digit, which in particular characterizes the sealing of the beam exit window in the housing. If, for example, a degree of protection of 6 "protection against strong jets of water" has to be met here, the required code number is "IP66."

BACKGROUND ART

The reduction of the microbial load depends on the radiation dose arriving at the substrate. This is determined by the irradiation power of the UV lamp module and the period during which the substrate is exposed to the UV radiation. In systems in which the substrate is moved along the UV lamp module, a prolongation of the irradiation period is obtained by the fact that multiple UV lamps are assembled in a UV lamp module to form a flat, planar arrangement.

An embodiment of a UV lamp module of this type, designed for use in a disinfection system with a disinfection station, is described in DE 20 2017 101 112 UL, from which a UV lamp module according to the type mentioned above is also known.

In a metal housing, a total of eight UV lamps in the form of low-pressure mercury lamps are arranged, each having a lamp casing tube with a circular cross-section. The longitudinal axes of the lamps extend in parallel and in a common lamp plane, so that overall they form a planar lamp arrangement.

The metal housing has an upwardly curving housing upper part, to which a housing lower part is screwed, in which a fused silica pane is held as a beam exit window. The fused silica pane rests on a peripheral shoulder by way of a sealing ring and is pressed on to the sealing ring by a mechanical holding-down device. This seal easily withstands cleaning cycles with strong jets of water, as is conventional, e.g., in food industry facilities, and so the lamp module is suitable for long-term use under the IP66 Hygiene Standard.

Technical Problem

The UV lamp module is arranged in the disinfection system such that, at least in an irradiation area, an irradiation of the substrate takes place with a predefined minimum irradiation dose. From the point of view of costs there is a tendency, and for space-related reasons often even a requirement, to keep the number of UV lamps as low as possible in favor of using powerful UV lamps.

However, the overall efficiency of the disinfection system is substantially determined by the homogeneity of the radiation field, since a local increase in the irradiation intensity is not generally harmful but a locally reduced intensity is, as it can lead to inadequate treatment. In the interests of high decontamination efficiency, therefore, it is helpful for the distribution of the radiation intensity to be as homogeneous as possible.

The requirements relating on the one hand to the compactness of the UV lamp module, because available installation space is small, and on the other hand to the homogeneity and thus the efficiency of the UV irradiation, are therefore conflicting in nature and not easily met simultaneously.

In addition, when the lamp module is used in food industry processes, hygiene standards have to be maintained such as for instance the USA's 3A certification ("AAA Hygienic Design" or "3-A Sanitary Standards"), the EHEDG (European Hygienic Engineering and Design Group) guideline or the standard DIN EN 1672-2, in which design details of the appropriate accessories connected with the production, cleaning and packaging of consumable products are specified. The choice of materials, surface finish, precision in manufacture, position and number of weld seams and gap size play an important role here.

It is therefore an object of the present invention to improve a UV lamp module of the type mentioned above in terms of maintaining hygiene standards and, at the same time, with regard to homogeneity and compactness.

Furthermore, the invention is based on the object of specifying a suitable use of the UV lamp module.

SUMMARY OF THE INVENTION

These and other objects are achieved according to the invention in that a first airflow zone for the supply of cooling air and a second airflow zone, which is in particular fluidically separated from the first airflow zone, for the discharge of heated cooling air are formed in the housing, wherein, viewed in a cross-section through the housing perpendicular to the longitudinal axes of the low-pressure mercury lamps and in a direction from the bottom side to the top side, the beam exit window, the lamp arrangement and the airflow zones are arranged one after the other, and wherein the first airflow zone comprises an air supply duct which is equipped with at least one air-guiding mechanism for supplying cooling air to the lamp arrangement.

In the UV lamp module according to the invention, the following aspects in particular are advantageous:

1. At least some of the UV lamps in the lamp arrangement, preferably all the lamps in the lamp arrangement, are low-pressure mercury lamps. Low-pressure mercury lamps have higher energy efficiency compared to medium-pressure mercury lamps or high-pressure mercury lamps. Furthermore, they display higher decontamination efficiency in the sense that the fraction of UV radiation in the wavelength range of about 254 nm in the overall emission spectrum is comparatively large. UV radiation in the wavelength range of about 254 nm proves particularly effective in decontamination.

2. For cooling the lamp arrangement, the housing has an air supply duct for the supply of cooling air and therefore a connection to a cooling air source. In principle, a cooling of low-pressure mercury lamps is not necessary. However, the cooling that can be switched on in the LI lamp module according to the invention proves to be beneficial in multiple respects for solving the aforementioned technical problem.

a. It enables low-pressure mercury lamps with comparatively high power to be used and operated without the risk of overheating of the lamp arrangement. In the event of overheating, there is a decrease in the spectral fraction of UV emission, accompanied by a reduction in UV irradiation power, in particular in the wavelength range of about 254 nm.

For example, in a particularly suitable embodiment of the UV lamp module according to the invention in which the longitudinal axes of the low-pressure mercury lamps extend in a common lamp plane, as a result of the use and operation of low-pressure mercury lamps with comparatively high power the lamp arrangement can be designed such that a LV irradiation intensity of at least 100 mW/cm2, preferably at least 120 mW/cm2, is produced measured at a distance of 48 mm from the lamp plane.

b. The risk of overheating of the planar lamp arrangement lies in particular in the area of its center, and less so in the marginal areas. By the forced cooling of the low-pressure mercury lamps by supplying cooling air, a comparatively homogeneous temperature profile can be established over the length and width of the lamp arrangement, accompanied by a locally homogeneous irradiation profile of the emitted UV radiation.

To avoid overheating of the lamp arrangement, the cooling performance of the cooling air is therefore preferably designed such that a maximum temperature of less than 150° C. particularly preferably less than 120° C., is established on the lamp arrangement.

3. The housing is closed and waterproof. The water impermeability corresponds to at least the degree of protection of 6 of the above-defined IP code; in other words, the housing can permanently withstand cleaning cycles with strong jets of water.

At least one air supply duct for the cooling air and at least one exhaust air duct for the discharge of the heated cooling air extend inside the housing. The cooling air passes via air-guiding mechanisms, such as one or more openings or lines, on to the lamp arrangement, which it cools and is thereby heated. Since the housing is closed, the entire volume of cooling air is discharged from the housing as heated cooling air via the exhaust air duct in a defined and reproducible manner, which represents an advantageous measure in terms of hygiene requirements.

The ducts are configured, e.g., as a hose or pipe and can be provided with connector elements at the housing exit. Air represents the simplest coolant from a technological viewpoint, and the cheapest. Naturally, other gases or even liquids can also be employed as coolants instead of or in addition to air.

4. The extension of the housing in the direction of the longitudinal axis of the low-pressure mercury lamps will be referred to below as the "housing length." the extension in the above-defined viewing direction as the "housing height," and the extension in the remaining spatial direction as the "housing width." These designations and also position indications used in connection with the description of the housing, such as "top side" or "bottom side," and adverbs of place such as "above." "one above the other." "top," "upper" and the like relate to the orientation of the housing illustrated in the exemplary embodiment; they serve only to define the relative orientation of components to one another and do not represent a specification of a particular spatial orientation of either the housing or the relevant components when used as intended.

The first airflow zone and the second airflow zone are in particular fluidically separated from each other inside the housing, so that no mixing of cooling air that is still cold and cooling air that is already heated occurs in the housing. The first airflow zone for the supply of the cold cooling air has an air supply duct, which in turn is equipped with at least one air-guiding mechanism for the defined supplying of cold cooling air on to the lamp arrangement. The heated cooling air passes as exhaust air by way of the second airflow zone to an exhaust air duct or to a gas outlet, by way of which it is discharged from the housing.

Viewed in the direction of the housing height, the first and second airflow zones extend one above the other over at least part of the housing length. Preferably, viewed in a cross-section through the housing perpendicular to the longitudinal axes of the low-pressure mercury lamps and in a viewing direction from the bottom side to the top side, the first airflow zone is arranged upstream of the second airflow zone. In other words, the air supply duct transporting the cooling air extends close to the lamp arrangement, so that the cooling air can be discharged from the air supply duct towards the lamp arrangement comparatively simply by way of the air-guiding mechanism.

Owing to the "stacked" arrangement of the beam exit window, the lamp arrangement and the two airflow zones, the following four planes, arranged one above the other, are obtained schematically over at least part of the housing length:

(i) The window plane, in which the beam exit window is arranged.

(ii) The lamp plane, in which the longitudinal axes of the low-pressure mercury lamps extend;

(iii) The lower airflow plane, in which preferably the longitudinal axis of the air supply duct extends; and (iv) The upper airflow plane, in which preferably the longitudinal axis of an exhaust air duct or a housing gas outlet extends.

The above-mentioned planes can extend obliquely to one another, but in the preferred case they extend parallel to one another. The "stacked" arrangement of these components adds to the housing height, but enables a particularly low housing width to be achieved. The comparatively low housing width may be helpful in tight installation spaces and contributes to the homogeneity of the radiation in the irradiation area, especially when multiple UV lamp modules are arranged one after the other in the direction of transport of the substrate.

Particularly with a view to a housing width that is as low as possible and the accompanying high homogeneity of the radiation field with such an arrangement of multiple UV lamp modules one behind another, the following embodiments of the UV lamp module are also preferred:

(a) Embodiments in which the air supply duct has an air supply duct central axis and the second airflow zone has an exhaust air duct central axis, wherein the air supply duct central axis and the exhaust air duct central axis extend parallel to one another in a common housing central plane, which extends perpendicular to the beam exit window.

The exhaust air duct central axis corresponds to the longitudinal axis of a possible exhaust air duct or the central axis of a housing gas outlet. Not only do the airflow zones for supply air and exhaust air extend one after the other, seen in the viewing direction, but the axes of the air supply duct and the exhaust air duct or gas outlet also extend one above the other in the housing central plane. This results in a particularly low housing width.

(b) Embodiments in which the housing exhibits mirror symmetry in relation to the housing central plane.

(c) Embodiments in which the first airflow zone has an air supply duct inner diameter and the second airflow zone has an exhaust air duct inner diameter, wherein the exhaust air duct inner diameter differs by less than +/−10% from the air supply duct inner diameter, and preferably the exhaust air duct inner diameter and the air supply duct inner diameter are identical.

Where the inner diameters are identical, the same flow velocities for cooling air and exhaust air and the same gas pressures are obtained. A smaller exhaust air duct inner diameter, on the other hand, would lead to a greater flow resistance than in the air supply duct and would act as a bottleneck for the cooling air stream.

In a particularly advantageous embodiment of the UV lamp module, the housing top side exhibits a curvature, specifically in the cross-section through the housing perpendicular to the longitudinal axes of the low-pressure mercury lamps.

The outwardly curved housing top side facilitates the flow of liquid off the housing, e.g., during cleaning of the lamp module. This measure facilitates residue-five cleaning and contributes to maintaining and improving the hygiene standard.

The effect of the curved top side in terms of the residue-free cleaning of the lamp module is further enhanced if the two side walls fit closely with the curvature of the top side, together forming an angle in the range of between 5 and 40 degrees (in their imaginary elongation).

For the impermeability of the housing to splash water, the attachment of the beam exit window to the housing is particularly crucial. In DE 20 2017 101 112 UI, which has already been cited above, mechanical measures are proposed for this purpose, but these are complex. In another preferred embodiment of the UV lamp module according to the invention, impermeability is ensured by the fact that the beam exit opening has a peripheral shoulder to which the beam exit window is adhesively bonded.

In a further advantageous embodiment of the IN lamp module according to the invention, the lamp arrangement is at least partially surrounded by a reflector on its side facing away from the bean exit window.

The reflector extends in the direction of the housing length and the housing width between the lamp plane and the bottom air duct plane, preferably completely covering the lamp arrangement. It contributes to increasing the irradiation intensity and improves the homogeneity of the radiation field.

In a further embodiment of the UV lamp module according to the invention, at least one of the housing side walls has a visible side that is provided with a marking, wherein the marking is created by laser engraving and then the visible side is polished by electropolishing.

The electropolishing removes any residues from the creation of the marking and contributes to the improvement in terms of the hygiene standard. It has been shown that the sequence of method steps in the order of laser engraving and electropolishing after the electropolishing a surface with a different finish from that on the non-engraved surface is obtained in the region of the engraving, so that the marking remains visible. The marking of the visible side comprises, e.g., lettering, a logo or numbers.

With regard to the use of the UV lamp module according to the invention, the above-mentioned objects are achieved according to the invention by the fact that it is employed in a disinfection system for the ultraviolet irradiation of packaging material for food or medicines. Preferably in this case, the UV lamp module is employed in a set of modules in which multiple structurally identical UV lamp modules are arranged one after the other, viewed in the direction of transport of a substrate to be irradiated.

It is to be understood that both the foregoing general description and the following detailed description are exemplary, but are not restrictive, of the disclosure.

BRIEF DESCRIPTION OF THE DRAWINGS

The invention will be explained in more detail below with reference to drawings and exemplary embodiments. The individual figures of the drawings show the following.

DETAILED DESCRIPTION

Figure 1:
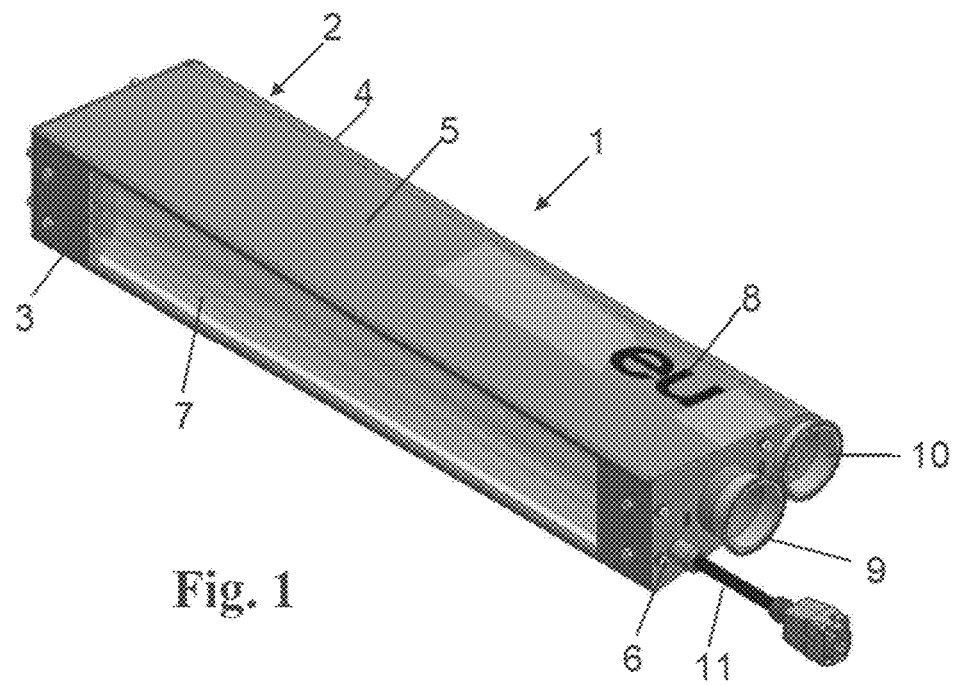
FIG. 1 shows an exemplary embodiment of the UV lamp module according to the invention in a spatial illustration.

The embodiment of the UV lamp module 1 of FIG. 1 has a metallic housing 2 with a bottom side 3, an outwardly curved top side 4, two flat side walls 5 and two closing walls 6 opposite each other at the ends. The housing length is about 1,050 mm, the housing height about 300 nm and the maximum housing width on the bottom side 3 is about 160 mm.

The largest part of the bottom side 3 is taken up by a rectangular opening, which is sealed in a waterproof manner by a beam exit window 7 in the form of a fused silica plate with dimensions of 856×142 mm.

The curvature of the top side 4 has a radius of about 90 mm and extends over the entire housing length from one closing wall 6 to the other.

The two flat side walls 5 extend from the bottom side 3 to the top side 4 and fit closely with the curvature thereof. They extend towards each other at an oblique angle, forming an angle of 14 degrees with each other in their imaginary elongation. The side walls 5 and the curved top side 4 are made from a piece of sheet metal. On the visible side of one side wall 5, lettering 8 has been engraved by laser and then the side wall 5 has been completely electropolished.

Figure 2:
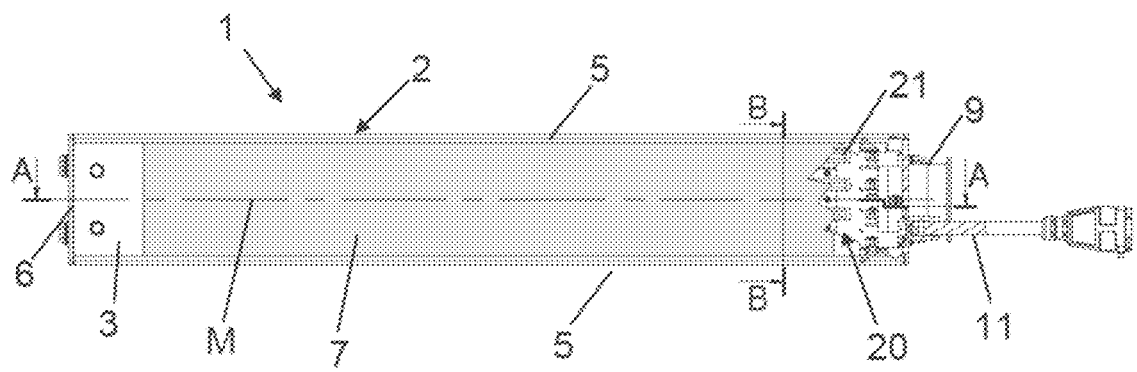
FIG. 2 shows a technical drawing of the UV lamp module in a top view of the beam exit widow, including a partial cutaway with a view of the lamp arrangement.

A lower connector 9 of an air supply duct (FIG. 3; reference number 31) for the supply of cooling air into the housing 2 and a further, upper, connector 10 of an exhaust air duct (FIG. 3; reference number 32) for the discharge of heated cooling air from the housing 2 protrude from one closing wall 6. From the same closing wall 6 a cable is also fed out for the electrical connection of four UV lamps 21, which are visible from the view of FIG. 2.

Figure 3:
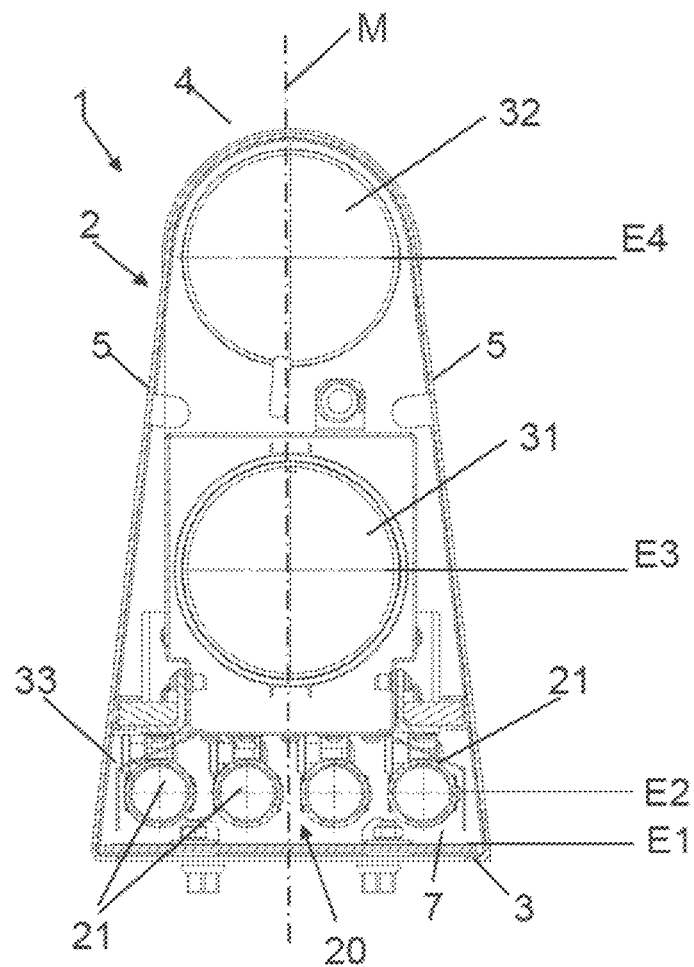
FIG. 3 shows the UV lamp module in a cross-section along the line B-B of FIG. 2 in an enlarged illustration.

The UV lamps 21 are low-pressure mercury lamps with a cylindrical lamp tube composed of fused silica and electrodes arranged opposite each other therein. The lamp tube has an outer diameter of 28 mm and is sealed in a gas-tight manner at both ends by a pinch seal, through which the power connections for the electrical bonding of the electrodes are fed in a conventional manner. The lamp tube is filled with a mercury amalgam and neon; each lamp tube has an amalgam deposit. The UV lamps 21 form a planar lamp arrangement 20, in which the longitudinal axes of the lamps 21 extend parallel to one another and in a common plane (FIG. 3; lamp plane E2). The lamp arrangement 21 extends evenly on both sides of a mirror plane M of the housing 2 (more readily visible in FIG. 3). The distance between the longitudinal axes of the lamps 21 is 36 mm. The nominal connected load of the individual mercury vapor discharge lamps is 580 W. The radiant flux can be up to 150 W. The low-pressure mercury lamps 21 display an emission spectrum with high efficiency of the characteristic emission line at 254 nm. At a distance of 48 mm from the lamp plane E2 (i.e., 20 mm below the bottom side 3 of the housing 2), a U V irradiation intensity of 140 mW/cm2 is obtained.

From the sectional illustration of FIG. 3, the vertical arrangement of the essential components of the LV lamp module 1 inside the housing 2 can readily be seen. The top side of the beam exit window 7 extends in the window plane E1 and above it the planar arrangement 20 of the four UV lamps 21, the longitudinal axes of which span the lamp plane E2. The distance between the planes E1 and E2 is 21 mm. The arrangement 20 of the UV lamps 21 is surrounded at the top and sides by a reflector sheet 33 with a trapeziform profile. Above them extends the air supply duct 31 for the cooling air, the central axis of which defines the horizontal plane E3. And above this extends the exhaust air duct 32, which is configured only as a short connector with a length of 2 cm and the central axis of which defines the horizontal plane E4.

Figure 4:
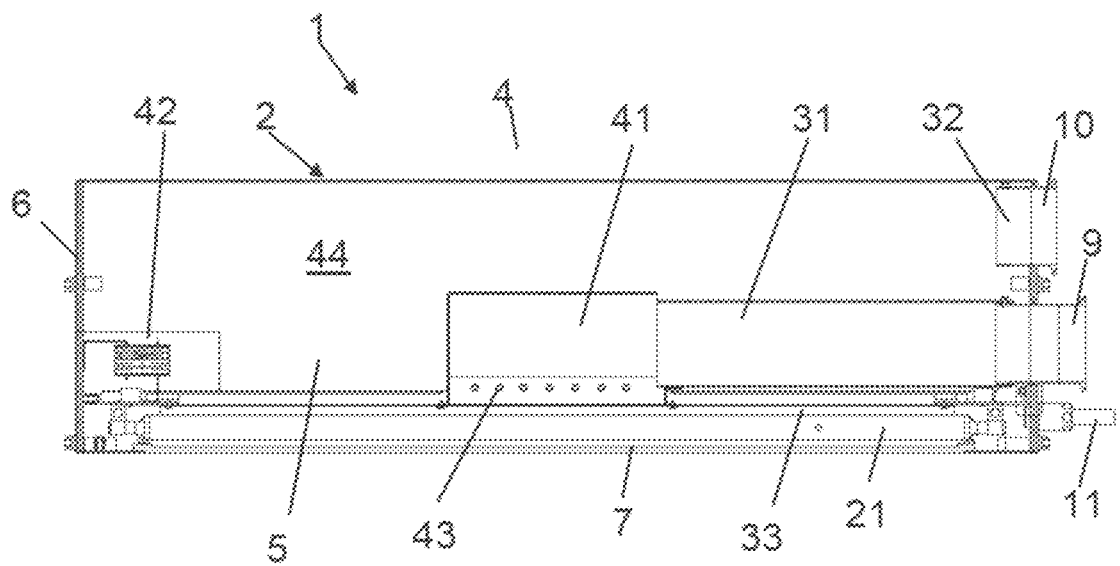
FIG. 4 shows the UV lamp module in a longitudinal section along the line A-A of FIG. 2 partially m section.

The housing 2 is substantially symmetrical relative to the mirror plane M. The beam exit window 7 has a sheet thickness of 4 min; it rests against a folded edge of the side walls 5 and is adhesively bonded thereto in a waterproof manner. The reflector sheet 33 extends over the entire length of the UV lamp arrangement 20. The air supply duct 31 has an inner diameter of 85 mm. Its central axis lies in the mirror plane M. It extends along the housing length from the lower connector 9 to a gas distribution chamber 41 arranged in the middle of the housing 2 (FIG. 4). The exhaust air duct 32 also has an inner diameter of 85 mm, and its central axis is likewise in the mirror plane M. It can be seen that the exhaust air duct 32 defines the curvature of the housing top side 4 and almost completely fills it.

It can be seen from the view of FIG. 4 that the air supply duct 31 leads into the gas distribution chamber 41. The gas distribution chamber 41 is provided on its side facing the reflector sheet 33 with a plurality of openings 43, through which the cooling air flows into the space in which the arrangement 20 of the UV lamps 21 is located. At the openings 43 of the gas distribution chamber 41 a first airflow zone terminates, which determines the airflow of the cold cooling air from the air supply duct lower connector 9 to the lamp arrangement 20.

The airflow of the heated cooling air to the exhaust air duct upper connector 10 is defined by a second airflow zone. Here, the heated cooling air volume, starting from the lamp arrangement 20, is supplied by way of the free internal space 44 of the housing 2 to the end of the exhaust air duct 32 that protrudes into the housing 2, and is removed completely from the housing 2 by way of the exhaust air duct upper connector 10. No mixing with cold cooling air takes place here, since the second airflow zone is in particular fluidically separated from the first airflow zone.

The cooling performance of the cooling air is designed such that a maximum temperature of less than 110° C. is obtained on the lamp arrangement 20. And to achieve a distribution of the UV irradiation profile that is locally as homogeneous as possible, the cooling performance and the local distribution of the cooling air are designed such that a temperature difference of less than 10° C. is obtained between the maximum temperature and the minimum temperature at the mercury deposits of the individual low-pressure mercury lamps 21 of the lamp arrangement 20.

For the simple maintenance and replacement of the low-pressure mercury lamps 21, the UV lamp module 1 can be opened in the manner of a drawer. In this case the metal housing 2, including one of the two end closing walls 6 and the beam exit window 7, remains firmly in place. It is the opposite end closing wall 6 provided with a connection cable 11 that is pulled out, with the mechanically connected components such as the low-pressure mercury lamps 21, the gas distribution chamber 41 and the air supply duct 31. The end of the "drawer" protruding into the housing 2 is provided with an electrical plug, which joins to a corresponding socket in a mount 42 when pushed back in to form an electrical plug connection.

The lamp module 1 according to the invention also meets strict requirements of the above-mentioned hygiene standards and achieves the degree of sealing according to IP66.

Figure 5:
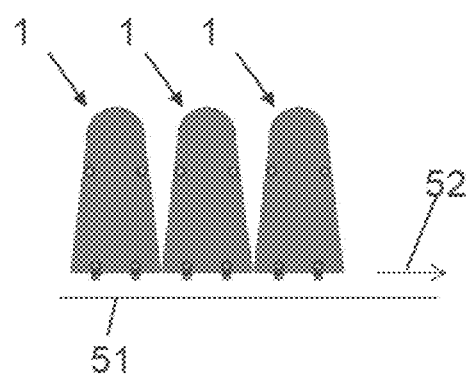
FIG. 5 shows a series of juxtaposed UV lamp modules in a schematic illustration.

When structurally identical UV lamp modules 1 are arranged in a closely juxtaposed series (theoretically without a gap; although in practice a small gap is useful so that liquid can drain), as illustrated schematically in FIG. 5, a clearance of only 13.7 mm is obtained between the UV lamps 21 of adjacent modules 1 and a distance between the central axes of 55.4 mm exists. The UV lamp module 1 according to the invention is therefore particularly suitable for use in a disinfection system for the ultraviolet irradiation of a packaging material 51 for food or medicines. In this case, multiple UV lamp modules 1 are arranged one after the other in a direction of transport 52 of the packaging material 51 to be irradiated, in such a way that the central axes of the low-pressure mercury lamps 21 extend parallel to one another and transverse to the direction of transport 52.

Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure.

The invention claimed is:

1. A UV lamp module for the ultraviolet irradiation of a substrate, comprising:
   a lamp arrangement that includes multiple low-pressure mercury lamps each having a longitudinal axis;
   a waterproof housing surrounding the lamp arrangement and having a bottom side, a top side and at least two side walls connecting the bottom side and the top side to each other, and a beam exit opening on the bottom side which is closed by a beam exit window;
   a first airflow zone formed in the housing and having an air supply duct with at least one air-guide for the supply of cooling air to the lamp arrangement; and
   a second airflow zone, which is separated from the first airflow zone, formed in the housing for the discharge of heated cooling air and having an exhaust air duct,
   wherein, viewed in a cross-section through the housing perpendicular to the longitudinal axes of the low-pressure mercury lamps and in a viewing direction from the bottom side to the top side, the beam exit window, the lamp arrangement and the airflow zones are arranged one after the other, and
   wherein the air supply duct has a first central axis and the exhaust air duct has a second central axis, and the first central axis and the second central axis extend parallel to one another in a common housing central plane which extends perpendicular to the beam exit window.

2. The UV lamp module according to claim 1, wherein, viewed in the cross-section through the housing perpendicular to the longitudinal axes of the low-pressure mercury lamps and in a viewing direction from the bottom side to the top side, the first airflow zone is arranged upstream of the second airflow zone.

3. The UV lamp module according to claim 1, wherein the housing has a central plane and exhibits mirror symmetry in relation to the housing central plane.

4. The UV lamp module according to claim 1, wherein the air supply duct of the first airflow zone has an inner diameter and the second airflow zone has an exhaust air duct with an inner diameter, and the exhaust air duct inner diameter differs by less than +/−10% from the air supply duct inner diameter.

5. The UV lamp module according to claim 1, wherein in a cross-section through the housing perpendicular to the longitudinal axes of the low-pressure mercury lamps the housing top side exhibits a curvature.

6. The UV lamp module according to claim 5, wherein the at least two side walls fit closely with the curvature of the top side and form an angle with each other in the range of between 5 and 40 degrees.

7. The UV lamp module according to claim 1, wherein the beam exit opening has a peripheral shoulder, to which the beam exit window is adhesively bonded.

8. The UV lamp module according to claim 1, wherein the longitudinal axes of the low-pressure mercury lamps extend in a common lamp plane and the lamp arrangement is configured to produce a UV irradiation intensity of at least 100 mW/cm$^2$ on the substrate measured at a distance of 48 mm from the lamp plane.

9. The UV lamp module according to claim 1, further comprising a reflector and wherein the lamp arrangement has a side facing away from the beam exit window and is at least partially surrounded by the reflector on its side facing away from the beam exit window.

10. The UV lamp module according to claim 1, wherein at least one of the housing side walls has a visible side provided with a marking created by laser engraving, and then the visible side has been polished by electropolishing.

11. The use of a UV lamp module according to claim 1 in a disinfection system for the ultraviolet irradiation of packaging material for food or medicines.

12. The UV lamp module according to claim 4, wherein the exhaust air duct inner diameter and the air supply duct inner diameter are identical.

13. A UV lamp module for the ultraviolet irradiation of a substrate, comprising:
   a lamp arrangement that includes multiple low-pressure mercury lamps each having a longitudinal axis;
   a waterproof housing surrounding the lamp arrangement and having a bottom side, a top side and at least two side walls connecting the bottom side and the top side to each other, and a beam exit opening on the bottom side which has a peripheral shoulder and is closed by a beam exit window adhesively bonded to the peripheral shoulder;
   a first airflow zone formed in the housing and having an air supply duct with at least one air-guide for the supply of cooling air to the lamp arrangement; and
   a second airflow zone, which is separated from the first airflow zone, formed in the housing for the discharge of heated cooling air,
   wherein, viewed in a cross-section through the housing perpendicular to the longitudinal axes of the low-pressure mercury lamps and in a viewing direction from the bottom side to the top side, the beam exit window, the lamp arrangement and the airflow zones are arranged one after the other and the first airflow zone is arranged upstream of the second airflow zone,
   wherein the air supply duct of the first airflow zone has a central axis and the second airflow zone has an exhaust air duct with a central axis, and the air supply duct central axis and the exhaust air duct central axis extend parallel to one another in a common housing central plane which extends perpendicular to the beam exit window, wherein the air supply duct of the first airflow zone has an inner diameter and the second airflow zone has an exhaust air duct with an inner diameter, and the exhaust air duct inner diameter differs by less than +/−10% from the air supply duct inner diameter, wherein in a cross-section through the housing perpendicular to the longitudinal axes of the low-pressure mercury lamps the housing top side exhibits a curvature, and wherein the longitudinal axes of the low-pressure mercury lamps extend in a common lamp plane and the lamp arrangement is configured to produce a UV irradiation intensity of at least 100 mW/cm$^2$ on the substrate measured at a distance of 48 mm from the lamp plane, and wherein at least one of the housing side walls has a visible side provided with a marking created by laser engraving, and then the visible side has been polished by electropolishing.

14. The UV lamp module according to claim 13, wherein the housing has a central plane and exhibits mirror symmetry in relation to the housing central plane.

15. The UV lamp module according to claim 13, wherein the exhaust air duct inner diameter and the air supply duct inner diameter are identical.

16. The UV lamp module according to claim 13, wherein the at least two side walls fit closely with the curvature of the top side and form an angle with each other in the range of between 5 and 40 degrees.

17. The UV lamp module according to claim 13, further comprising a reflector and wherein the lamp arrangement has a side facing away from the beam exit window and is at least partially surrounded by the reflector on its side facing away from the beam exit window.

18. The use of a UV lamp module according to claim 13 in a disinfection system for the ultraviolet irradiation of packaging material for food or medicines.

19. A UV lamp module for the ultraviolet irradiation of a substrate, comprising:

a lamp arrangement that includes multiple low-pressure mercury lamps each having a longitudinal axis;

a waterproof housing surrounding the lamp arrangement and having a bottom side, a top side and at least two side walls connecting the bottom side and the top side to each other, and a beam exit opening on the bottom side which is closed by a beam exit window;

a first airflow zone formed in the housing and having an air supply duct with at least one air-guide for the supply of cooling air to the lamp arrangement; and a second airflow zone, which is separated from the first airflow zone, formed in the housing for the discharge of heated cooling air, wherein, viewed in a cross-section through the housing perpendicular to the longitudinal axes of the low-pressure mercury lamps and in a viewing direction from the bottom side to the top side, the beam exit window, the lamp arrangement and the airflow zones are arranged one after the other, and wherein at least one of the housing side walls has a visible side provided with a marking created by laser engraving, and then the visible side has been polished by electropolishing.

* * * * *